US007270955B2

(12) United States Patent
Evans et al.

(10) Patent No.: US 7,270,955 B2
(45) Date of Patent: Sep. 18, 2007

(54) TRANSCRIPTIONAL CO-REPRESSOR THAT INTERACTS WITH NUCLEAR HORMONE RECEPTORS AND USES THEREFOR

(75) Inventors: Ronald M. Evans, La Jolla, CA (US); J. Don Chen, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 729 days.

(21) Appl. No.: 10/351,750

(22) Filed: Jan. 23, 2003

(65) Prior Publication Data

US 2003/0138836 A1 Jul. 24, 2003

Related U.S. Application Data

(62) Division of application No. 09/337,384, filed on Jun. 21, 1999, now Pat. No. 6,551,773, which is a division of application No. 08/522,726, filed on Sep. 1, 1995, now Pat. No. 6,489,441.

(51) Int. Cl.
*C12Q 1/68* (2006.01)
*G01N 33/567* (2006.01)
*C12N 15/36* (2006.01)

(52) U.S. Cl. .......................... 435/6; 435/7.2; 435/7.21

(58) Field of Classification Search ...................... None
See application file for complete search history.

(56) References Cited

U.S. PATENT DOCUMENTS

| 4,981,784 A | 1/1991 | Evans et al. |
| 5,071,773 A | 12/1991 | Evans et al. |
| 5,091,518 A | 2/1992 | Sucov et al. |
| 5,260,432 A | 11/1993 | Takaku et al. |

OTHER PUBLICATIONS

Ayer et al., "Mad-Max Transcriptional Repression is Mediated by Ternary Complex Formation with Mammalian Homologs of Yeast Repressor Sin3" *Cell* 80:767-776 (1995).
Bahouth et al. "Immunological Approaches for Probing Receptor Structure and Function" *TIPS Reviews* 12:338-343 (1991).
Baniahmad et al., "Modular Srurcture of a Chicken Lysozyme Silencer: Involvement of an Unusual Thyroid Hormone Receptor Binging Site" *Cell* 61:505-514 (1990).
Baniahmad et al., "Kindred S Thyroid Hormone Receptor is an Active and Constitutive Silencer and a Repressor for Thyroid Hormone and Retinoic Acid Response" *Proc. Natl. Acad. Sci. USA* 89:10633-10637 (1992).
Baniahmad et al., "A Transferable Silencing Domain is Present in the Thyroid Hormone Receptor, in the v-erbA Oncogene Product and in the Retinoic Acid Receptor" *EMBO J.* 11(3):1015-1023 (1992).
Baniahmad et al., "Interaction of Human Thyroid Hormone Receptor β with Transcription Factor TFIIB May Mediate Target Gene Derepression and Activation by Thryoid Hormone" *Proc. Natl. Acad. Sci. USA* 90:8832-8836 (1993).

Baniahmad et al., "The $_T$4 Activation Domain of the Thyroid Hormone Receptor is Required for Release of a Putative Corepressor(s) Necessary for Transcriptional Silencing" *Mol. Cell. Biol.* 15(1):76-86 (1995).
Barlow et al., "Thyroid Abnormalities and Hepatocellular Carcinoma in Mice Transgenic for v-erbA" *EMBO J.* 13:4241-4250 (1994).
Berger et al., "Interaction of Glucocorticoid Analogues with the Human Glucocorticoid Receptor" *J. Steroid Biochem. Molec. Biol.* 41(3-8):733-738 (1992).
Bourguet et al., "Crystal Structure of the Ligand-Binding Domain of the Human Nuclear Receptor RXR-α" *Nature* 377-382 (1995).
Brent et al., "Thyroid Hormone Aporeceptor Represses T3-Inducible Promoters and Blocks Activity of the Retinoic Acid Receptor" *New Biol.* 1(3):329-336 (1989).
Bugge et al., "RXRα, a Promiscuous Partner of Retinoic Acid and Thyroid Hormone Receptors" *EMBO J.* 11(4):1409-1418 (1992).
Casanova et al., "Functional Evidence for Ligand-Dependent Dissociation of Thyroid Hormone and Retinoic Acid Receptors from an Inhibitory Cellular Factor" *Mol. Cell. Biol.* 14(9) :5756-5765 (1994).
Cavaillès et al., "Interaction of Proteins with Transcriptionally Active Estrogen Receptors" *Proc. Natl. Acad. Sci. USA* 91:10009-10013 (1994).
Damm et al., "Protein Encoded by v-erbA Function as a Thyroid-Hormone Receptor Antagonist" *Nature* 339(6226) :593-597 (1989).
Damm et al., "Functional Inhibition of Retinoic Acid Response by Dominant Negative Retinoic Acid Receptor Mutants" *Proc. Natl. Acad. Sci. USA* 90 :2989-2993 (1993).
Damm and Evans, "Identification of a Domain Required for Oncogenic Activity and Transcriptional Suppression by v-erbA and Thyroid-Hormone Receptor α" *Proc. Natl. Acad. Sci. USA* 90:10668-10672 (1993).
Durfee et al. "The Retinoblastoma Protein Associates with the Protein Phosphatase Type 1 Catalytic Subunit" *Genes & Dev.* 7:555-569 (1993).

(Continued)

*Primary Examiner*—David Guzo
*Assistant Examiner*—Michele K. Joike
(74) *Attorney, Agent, or Firm*—Foley & Lardner LLP; Stephen E. Reiter

(57) ABSTRACT

In accordance with the present invention, there are provide novel receptor interacting factors, referred to herein as "SMRT", i.e., a silencing mediator (co-repressor) for retinoic acid receptor (RAR) and thyroid hormone receptor (TR). SMRT is a novel protein whose association with RAR and TR both in solution and on DNA response elements is destabilized by ligand. The interaction of SMRT with mutant receptors correlates with the transcriptional silencing activities of receptors. In vivo, SMRT functions as a potent co-repressor. A GAL4 DNA binding domain (DBD) fusion of SMRT behaves as a frank repressor of a GAL4-dependent reporter. Together, these data identify a novel class of cofactor which is believed to represent an important mediator of hormone action.

5 Claims, 3 Drawing Sheets

OTHER PUBLICATIONS

Fondall et al., "Unliganded Thyroid Hormone Receptor Inhibits Formation of a Functional Preinitiation Complex: Implications for Active Repression" *Genes & Dev.* 7:1400-1410 (1993).

Gandrillon et al., "Expression of the v-erbA Oncogen in Chicken Embryo Fibroblasts Stimulates Their Proliferation In Vitro and Enhances Tumor Growth In Vivo" *Cell* 49:687-697 (1987).

Halachmi et al., "Estrogen Receptor-Associated Proteins: Possible Mediators of Hormone-Induced Transcription" *Science* 264:1455-1458 (1994).

Hollenberg and Evans, "Multiple and Cooperative Trans-Activation Domains of the Human Glucocorticoid Receptor" *Cell* 55:899-906 (1988).

Kliewer et al., "Retinoid X Receptor Interacts with Nuclear Receptors in Retinoic Acid, Thyroid Hormone and Vitamin $D_3$ Signalling" *Nature* 355:446-449 (1992).

Le Douarin et al., "The N-terminal Part of TIF1, a Putative Mediator of the Ligand-Dependent Activation Function (AF-2) of Nuclear Receptors, is Fused to B-raf in the Oncogenic Protein T18" *EMBO J.* 14(9):2020-2033 (1995).

Lee et al., "Interaction of the Thyroid-Hormone Receptor with a Conserved Transcriptional Mediator" *Nature* 374:91-94 (1995).

Levine and Manley, "Transcriptional Repression of Eukaryotic Promoters" *Cell* 59:405-408 (1989).

Mangelsdorf et al., "Nuclear Receptor that Identified a Novel Retinoic Acid Response Pathway" *Nature* 345(6272):224-229 (1990).

Mangelsdorf et al., "A Direct Repeat in the Cellular Retinol-Binding Protein Type II Gene Confers Differential Regulation by RXR and RAR" *Cell* 66:555-561 (1991).

Muñoz et al. "Characterization of the Hormone-binding Domain of the Chicken c-erbA/Thyroid Hormone Receptor Protein" *EMBO J.* 7:155-159 (1988).

Saitou et al., "Inhibition of Skin Development by Targeted Expression of a Dominant-Negative Retinoic Acid Receptor" *Nature* 374:159-162 (1995).

Sap et al., "The c-erb-A Protein is a High-Affinity Receptor for Thyroid Hormone" *Nature* 324:635-640 (1986).

Sap et al., "Repression of Transcriptional Mediated at a Thyroid Hormone Response Element by the v-erb-A Oncogene Product" *Nature* 340:242-244 (1989).

Schreiber-Agus et al.,"An Amino-Terminal Domain of Mxil Mediates Anit-Myc Oncogenic Activity and Interacts with a Homolog of the Yeast Transcriptional Repressor SIN3" *Cell* 80:777-786 (1995).

Seol et al., "Isolation of Proteins That Interact Specifically with the Retinoid X Receptor: Two Novel Orphan Receptors" *Molecular Endocrinology* 9 (1):72-85 (1995).

Thompson et al., "Identification of a Novel Thyroid Hormone Receptor Expressed in the Mammalian Central Nervous System" *Science* 237:1610-1614 (1987).

Tsai et al., "A Mutated Retinoic Acid Receptor-α Exhibiting Dominant-Negative Activity Alters the Lineage Development of a Multipotent Hematopoietic Cell Line" *Genes & Dev.* 6:2258-2269 (1992).

Tsai and Collins, "A Dominant Negative Retinoic Acid Receptor Blocks Neutrophil Differentiation at the Promyelocyte Stage" *Proc. Natl. Acad. Sci. USA* 90:7153-7157 (1993).

Webster et al., "The Yeast $UAS_G$ is a Transcriptional Enhancer in Human HeLa Cells in the Presence of the GAL4 Trans-Activator" *Cell* 52:169-178 (1988).

Webster et al. "The Hormone-Binding Domains of the Estrogen and Glucocorticoid Receptors Contain an Inducible Transcription Activation Function" *Cell* 54:199-207 (1988).

Weinberger et al., "Domain Structure of Human Glucocorticoid Receptor and its Relationship to the v-*erb-A* Oncogene Product" *Nature* 318:670-672 (1985).

Weinberger et al., "The c-*erb-A* Gene Encodes a Thyroid Hormone Receptor" *Nature* 324:641-646 (1986).

Yang et al., "Characterization of DNA Binding and Retinoic Acid Binding Properties of Retinoic Acid Receptor" *Proc. Natl. Acad. Sci. USA* 88:3559-3563 (1991).

Yu et al., "RXRβ: A Coregulator That Enhances Binding of Retinoic Acid, Thyroid Hormone, and Vitamin D Receptors to Their Cognate Response Elements" *Cell* 67:1251-1266 (1991).

Zenke et al., "v-*erbA* Oncogene Activation Entails the Loss of Hormone-Dependent Regulator Activity of c-*erbA*" *Cell* 61:1035-1049 (1990).

Chen and Evans, A transcriptional co-repressor that interacts with nuclear hormone receptors. Nature, 377: 454-457, 1995.

Ordentlich et al., Unique forms of human and mouse nuclear receptor corepressor SMRT. Proc. Natl. Acad. Sci./USA, 96:2639-2644, 1999.

Smart et al., SMRTe, a silencing mediator for retinoid and thyroid hormone receptors-extended isoform that is more related to the nuclear receptor corepressor. Proc. Natl. Acad. Sci/USA, 96:3519-3524, 1999.

GenBank Accession No. NM_002900.1, GI: 4506452, Mar. 19, 1999.

GenBank Accession No. O75376, GI: 47117817, Feb. 7, 2006.

FIGURE 2

```
   1 MEAWDAHQDKEAFAAEAQKLQGDQQCWTSGLQFQVQQREVIKASQHAQDQ
  51 SAFSYAQQGHQLQLGLHDTARQVLQRQQTISNQQQLISSAKHQSVLERQI
 101 GAISQGMSVQLHVQYSEHAKAQVGQVTMGLQLQMDQKKLAQFSGVKQEQL
 151 SPRGQAGPPESLGVPTAQEASVLRGTALGSVPGGSITKGIPSTRVPSDSA
 201 ITYRGSITHGTPADVLYKGTITRIIGEDSPSRLDRGREDSLPKGHVIYEG
 251 KKGHVLSYEGGMSVTQCSKEDGRSSSGPPHETAAPKRTYDMMEGRVGRAI
 301 SSASIEGLMGRAIPPERHSPHHLKEQHHIRGSITQGIPRSYVEAQEDYLR
 351 REAKLLKREGTPPPPPPSRDLTEAYKTQALGPLKLKPAHEGLVATVKEAG
 401 RSIHEIPREELRHTPELPLAPRPLKEGSITQGTPLKYDTGASTTGSKKHD
 451 VRSLIGSPGRTFPPVHPLDVMADARALERACYEESLKSRPGTASSSGGSI
 501 ARGAPVIVPELGKPRQSPLTYEDHGAPFAGHLPRGSPVTMREPTPRLQEG
 551 SLSSSKASQDRKLTSTPREIAKSPHSTVPEHHPHPISPYEHLLRGVSGVD
 601 LYRSHIPLAFDPTSIPRGIPLDAAAAYYLPRHLAPNPTYPHLYPPYLIRG
 651 YPDTAALENRQTIINDYITSQQMHHNTATAMAQRADMLRGLSPRESSLAL
 701 NYAAGPRGIIDLSQVPHLPVLVPPTPGTPATAMDRLAYLPTAPQPFSSRH
 751 SSSPLSPGGPTHLTKPTTTSSSERERDRDRERDRDREREKSILTSTTTVE
 801 HAPIWRPGTEQSSGSSGSSGGGGGSSSRPASHSHAHQHSPISPRTQDALQ
 851 QRPSVLHNTGMKGIITAVEPSKPTVLRSTSTSSPVRPAATFPPATHCPLG
 901 GTLDGVYPTLMEPVLLPKEAPRVARPERPRADTGHAFLAKPPARSGLEPA
                                    ┌──► C-SMRT
 951 SSPSKGSEPRPLVPPVSGHATIARTPAKNLAPHHASPDPPAPPASASDPH
1001 REKTQSKPFSIQELELRSLGYHGSSYSPEGVEPVSPVSSPSLTHDKGLPK
1051 HLEELDKSHLEGELRPKQPGPVKLGGEAAHLPHLRPLPESQPSSSPLLQT
1101 APGVKGHQRVVTLAQHISEVITQDYTRHHQQLSAPLPAPLYSFPGASCP
1151 VLDLRRPPSDLYLPPPDHGAPARGSPHSEGGKRSPEPNKTSVLGGGEDGI
1201 EPVSPPEGMTEPGHSRSAVYPLLYRDGEQTEPSRMGSKSPGNTSQPPAFF

1251 SKQTESNSAMVKSKKQEINKKLNTHNRNEPEYNISQPGTEIFNMPAITGT

1301 GLMTYRSQAVQEHASTNMGLEAIIRKALMGKYDQW.EESPPLSANAFNPL

1350 NASASLPAAMPITAADGRSDHTLTSP].GGGGKAKVSGRPSSRKAKSPAPG

1399 LA..SGDRPPSVSSVHSEGDCNRRTPLTNRVWEDRPSSAGSTPFPYNPLT

1447 MRLQAGVMASPPPPGLPAGSGFL..AGPHHA...WDEEPKPLQCSQYETQ

1492 SDSE* 1495
```

US 7,270,955 B2

TRANSCRIPTIONAL CO-REPRESSOR THAT INTERACTS WITH NUCLEAR HORMONE RECEPTORS AND USES THEREFOR

RELATED APPLICATIONS

This application is a divisional application of U.S. patent application Ser. No. 09/337,384, filed Jun. 21, 1999 now U.S. Pat. No. 6,551,773, which is in turn a divisional application of U.S. patent application Ser. No. 08/522,726, filed on Sep. 1, 1995, now issued as U.S. Pat. No. 6,489,441, the entire contents of each of which are hereby incorporated by reference herein.

FIELD OF THE INVENTION

The present invention relates to intracellular receptors, methods for the modulation thereof, and methods for the identification of novel ligands therefor. In a particular aspect, the present invention relates to methods for the identification of compounds which function as ligands (or ligand precursors) for intracellular receptors. In another aspect, the present invention relates to novel chimeric constructs and uses therefor.

BACKGROUND OF THE INVENTION

A central problem in eukaryotic molecular biology continues to be the elucidation of molecules and mechanisms that mediate specific gene regulation. As part of the scientific attack on this problem, a great deal of work has been done in efforts to identify ligands (i.e., exogenous inducers) which are capable of mediating specific gene regulation. Additional work has been done in efforts to identify other molecules involved in specific gene regulation.

Although much remains to be learned about the specifics of gene regulation, it is known that ligands modulate gene transcription by acting in concert with intracellular components, including intracellular receptors and discrete DNA sequences known as hormone response elements (HREs).

The identification of compounds which directly or indirectly interact with intracellular receptors, and thereby affect transcription of hormone-responsive genes, would be of significant value, e.g., for therapeutic applications.

Transcriptional silencing mediated by nuclear receptors plays an important role in development, cell differentiation, and is directly linked to the oncogenic activity of v-erbA. The mechanism underlying this effect is unknown but is one key to understanding the molecular basis of hormone action. Accordingly, the identification of components involved in transcriptional silencing would represent a great advance in current understanding of mechanisms that mediate specific gene regulation.

Other information helpful in the understanding and practice of the present invention can be found in commonly assigned U.S. Pat. Nos. 5,071,773 and 4,981,784; and U.S. patent application Ser. No. 325,240, filed Mar. 17, 1989 (now issued as U.S. Pat. No. 5,597,693, based on continuation in part application Ser. No. 494,618, filed Mar. 16, 1990); Ser. No. 370,407, filed Jun. 22, 1989 (now issued as U.S. Pat. No. 5,260,432) and Ser. No. 438,757, filed Nov. 16, 1989 (now issued as U.S. Pat. No. 5,091,518), all of which are hereby incorporated herein by reference in their entirety.

BRIEF DESCRIPTION OF THE INVENTION

In accordance with the present invention, we have discovered a novel receptor interacting factor, referred to herein as "SMRT", i.e., a silencing mediator (co-repressor) for retinoic acid receptor (RAR) and thyroid hormone receptor (TR). SMRT is a novel protein whose association with RAR and TR both in solution and on DNA response elements is destabilized by ligand. The interaction of SMRT with mutant receptors correlates with the transcriptional silencing activities of receptors.

In vivo, SMRT functions as a potent co-repressor. A GAL4 DNA binding domain (DBD) fusion of SMRT behaves as a frank repressor of a GAL4-dependent reporter. Together, these data identify a novel class of cofactor which is believed to represent an important mediator of hormone action.

BRIEF DESCRIPTION OF THE FIGURES

FIG. 2 presents amino acid (aa) sequences of SMRT (Genbank accession number U37146; SEQ ID NO:1). The aa sequence presented in parentheses (i.e., residues 1330-1376) is an alternatively spliced insert which is not present in the original two-hybrid clone (C-SMRT, aa 981 to C-terminal end). The proline-rich N-terminal domain (aa 1-160) and the glutamine-rich region (aa 1061-1132), as well as the ERDR-rich and SG-rich regions (underlined), are also indicated. The C-terminal region of SMRT (aa 1201 to C-terminal end) shows 48% aa identity to RIP13 (Seol et al., *Molecular Endocrinology* 9:72-85 (1995)). The rest of the sequence of RIP13 shows 22% aa identity to SMRT (aa 819-1200)

FIG. 3(A) illustrates that v-erbA reverses the silencing effect of GAL-RAR (GAL4 DBD-hRARα 156-462) while SMRT restores the silencing effect.

FIG. 3(B) illustrates that the RAR403 truncation mutant reverses the silencing effect of GAL-TR (GAL4 DBD-hTRβ 173-456) while SMRT restores the silencing effect.

FIG. 3(C) illustrates that v-erbA and full length SMRT or C-SMRT have no effect on GAL-VP16 activity.

FIG. 3(D) illustrates that a GAL4 DBD fusion of full length SMRT suppresses the thymidine kinase basal promoter activity containing four GAL4 binding sites. The fold of repression was calculated by dividing the normalized luciferase activity transfected with the GAL4 DBD alone by those transfected with indicated amount of GAL DBD fusion constructs.

DETAILED DESCRIPTION OF THE INVENTION

Figure 1:
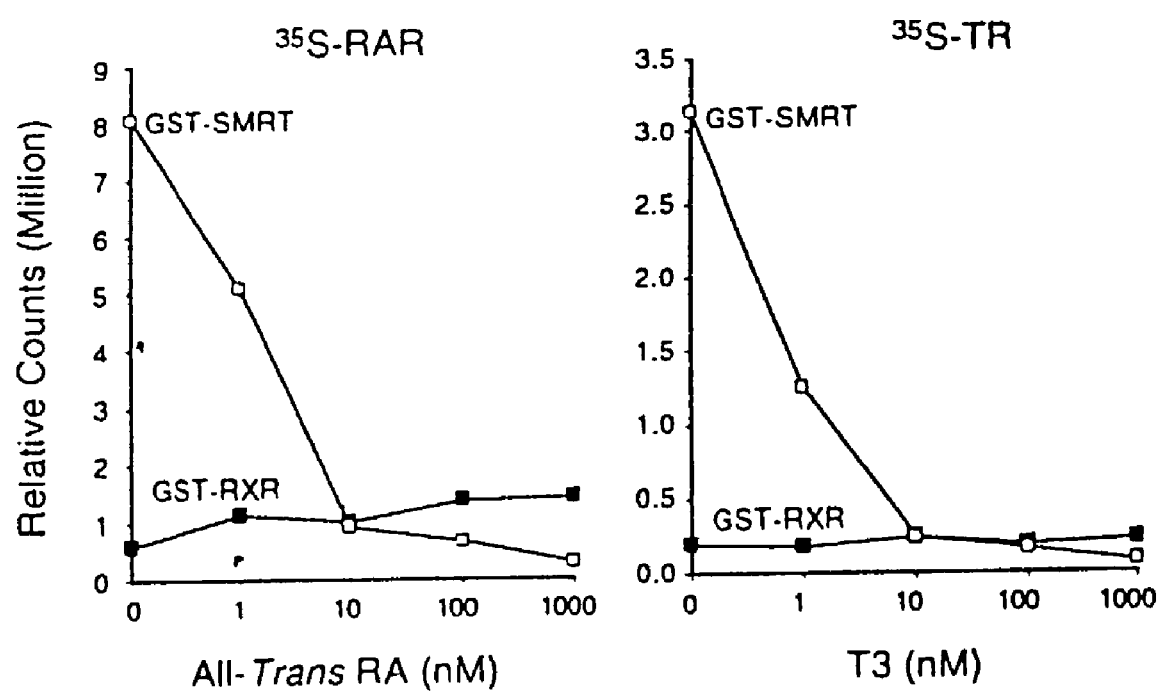
FIG. 1 shows the quantitation by phosphoimager of a dose-dependent dissociation of SMRT from RAR or TR by all-trans retinoic acid (atRA) or thyroid hormone (triiodothyronine or T3).

In accordance with the present invention, there are provided co-suppressors of steroid/thyroid hormone receptor activity, said co-suppressors having a structure and function characteristic of the silencing mediator for retinoic acid receptor and thyroid hormone receptor.

Co-suppressors contemplated by the present invention have substantially the same sequence as residues 1-1329 plus 1376-1495, as set forth in SEQ ID NO:1, optionally further comprising the amino acid residues set forth in SEQ ID NO:2 (i.e., residues 1330-1375 of SEQ ID NO:1).

The phrase "substantially the same" is used herein in reference to the nucleotide sequence of DNA, the ribonucleotide sequence of RNA, or the amino acid sequence of protein, that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the sequences disclosed and claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

In accordance with another aspect of the present invention, there are provided antibodies raised against the above-described co-suppressor. Such antibodies can be employed for studying tissue localization of invention co-repressor, the structure of functional domains, the purification of receptors, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention co-repressor or portions thereof as antigens for antibody production. Both anti-peptide and anti-fusion protein antibodies can be used [see, for example, Bahouth et al. (1991) *Trends Pharmacol Sci.* vol. 12:338-343; *Current Protocols in Molecular Biology* (Ausubel et al., eds.) John Wiley and Sons, New York (1989)]. Factors to consider in selecting portions of invention co-repressor for use as immunogen (as either a synthetic peptide or a recombinantly produced bacterial fusion protein) include antigenicity, accessibility (i.e., where the selected portion is derived from, e.g., the ligand binding domain, DNA binding domain, dimerization domain, and the like), uniqueness of the particular portion selected (relative to known receptors and co-suppressors therefor), and the like.

In accordance with yet another aspect of the present invention, there are provided methods to block the repressing effect of invention co-suppressors, said method comprising administering an effective amount of an antibody as described herein. Alternatively, a silencing domain of a nuclear receptor can be employed. Those of skill in the art can readily determine suitable methods for administering said antibodies, and suitable quantities for administration, which will vary depending on numerous factors, such as the indication being treated, the condition of the subject, and the like.

In accordance with a still further aspect of the invention, there are provided isolated polynucleic acids encoding the above-described co-suppressor. In addition, there are also provided vectors containing the above-described polynucleic acid.

In accordance with a still further aspect of the present invention, there are provided complexes comprising the above-described co-suppressor and a homodimeric or heterodimeric member of the steroid/thyroid hormone superfamily of receptors, wherein said member contains a silencing domain which represses basal level promoter activity of target genes. Homodimeric or heterodimeric members of the steroid/thyroid hormone superfamily of receptors contemplated for use herein include thyroid hormone receptor homodimer, thyroid hormone receptor-retinoid X receptor heterodimer, retinoic acid receptor homodimer, retinoic acid receptor-retinoid X receptor heterodimer, retinoid X receptor homodimer, and the like.

The above-described complexes optionally further comprise a response element for the member of the steroid/thyroid hormone superfamily of receptors. Such response elements are well known in the art. Thus, for example, RAR response elements are composed of at least one direct repeat of two or more half sites separated by a spacer of five nucleotides. The spacer nucleotides can independently be selected from any one of A, C, G or T. Each half site of response elements contemplated for use in the practice of the invention comprises the sequence

-RGBNNM-, wherein
R is selected from A or G;
B is selected from G, C, or T;
each N is independently selected from A, T, C, or G; and
M is selected from A or C;
with the proviso that at least 4 nucleotides of said -RGBNNM- sequence are identical with the nucleotides at corresponding positions of the sequence -AGGTCA-. Response elements employed in the practice of the present invention can optionally be preceded by $N_x$ wherein x falls in the range of 0 up to 5.

Similarly, TR response elements can be composed of the same half site repeats, with a spacer of four nucleotides. Alternatively, palindromic constructs as have been described in the art are also functional as TR response elements.

The above-described co-repressor/dimeric receptor complexes can be dissociated by contacting complex with a ligand for the member of the steroid/thyroid hormone superfamily of receptors.

As employed herein, the term "ligand (or ligand precursor) for a member of the steroid/thyroid hormone superfamily of receptors" (i.e., intracellular receptor) refers to a substance or compound which, in its unmodified form (or after conversion to its "active" form), inside a cell, binds to receptor protein, thereby creating a ligand/receptor complex, which in turn can activate an appropriate hormone response element. A ligand therefore is a compound which acts to modulate gene transcription for a gene maintained under the control of a hormone response element, and includes compounds such as hormones, growth substances, non-hormone compounds that modulate growth, and the like. Ligands include steroid or steroid-like hormone, retinoids, thyroid hormones, pharmaceutically active compounds, and the like. Individual ligands may have the ability to bind to multiple receptors.

Accordingly, as employed herein, "putative ligand" (also referred to as "test compound") refers to compounds such as steroid or steroid-like hormones, pharmaceutically active compounds, and the like, which are suspected to have the ability to bind to the receptor of interest, and to modulate transcription of genes maintained under the control of response elements recognized by such receptor.

Examples of known ligands include all-trans-retinoic acid (ligand for retinoic acid receptor), 9-cis-retinoic acid (ligand for retinoid X receptor), thyroid hormone (ligand for thyroid hormone receptor), 1,25-dihydroxy vitamin $D_3$ (ligand for vitamin $D_3$ receptor), and the like.

In accordance with another aspect of the present invention, there is provided a method to repress the activity of a member of the steroid/thyroid hormone superfamily of receptors containing a silencing domain which represses basal level promoter activity of target genes, said method comprising contacting said member of the steroid/thyroid hormone superfamily of receptors with a sufficient quantity of a co-suppressor as described hereinabove so as to repress the activity of said member. Members of the superfamily contemplated for repression in accordance with this aspect of the present invention include thyroid hormone receptor, retinoic acid receptor, vitamin D receptor, peroxisome proliferator activated receptor, and the like.

In accordance with yet another aspect of the present invention, there is provided a method to identify compounds which relieve the suppression of steroid/thyroid hormone receptor activity caused by a co-suppressor as described hereinabove, said method comprising comparing the size of the above-described co-suppressor/dimeric receptor complex (i.e., complexes comprising the above-described co-suppressor and a homodimeric or heterodimeric member of the steroid/thyroid hormone superfamily of receptors) upon exposure to test compound, relative to the size of said complex in the absence of test compound. An observed size corresponding to intact complex is indicative of an inactive compound, while an observed size that reflects dissociation of the complex is indicative of a compound that disrupts the complex, thereby relieving the suppression caused thereby. Optionally, the complex employed in this assay further comprises a response element for said member of the steroid/thyroid hormone superfamily of receptors.

The size of the above-described complex can readily be determined employing various techniques available in the art. For example, electrophoretic mobility shift assays (EMSA) can be employed (wherein receptor alone or receptor-co-suppressor complex is bound to target DNA and the relative mobility thereof determined). Those of skill in the art can readily identify other methodology which can be employed to determine the size of the complex as a result of exposure to putative ligand.

In accordance with a still further aspect of the present invention, there is provided a method to identify compounds which relieve the suppression of steroid/thyroid hormone receptor activity caused by a co-suppressor as described hereinabove, without substantially activating said receptor, said method comprising:

comparing the reporter signal produced by two different expression systems in the absence and presence of test compound,
wherein said first expression system comprises a complex comprising:
a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer, or retinoic acid receptor-retinoid X receptor heterodimer,
a response element for said member of the steroid/thyroid hormone superfamily of receptors, wherein said response element is operatively linked to a reporter, and
optionally, invention co-suppressor, and
wherein said second expression system comprises a complex comprising:
a homodimeric or heterodimeric form of the same member of the steroid/thyroid hormone superfamily of receptors as employed in said first expression system, wherein said member is mutated such that it retains hormone dependent activation activity but has lost its ability to repress basal level promoter activity of target genes,
the same response element-reporter combination as employed in said first expression system, and
optionally, invention co-suppressor, and thereafter selecting those compounds which provide:
a higher reporter signal upon exposure of said compound to said first expression system, relative to reporter signal in the absence of said compound, and
substantially the same reporter signal upon exposure of said compound to said second expression system, relative to reporter signal in the absence of said compound,
wherein said selected compounds are capable of relieving the suppression of steroid/thyroid hormone receptor activity caused by a co-suppressor having a structure and function characteristic of the silencing mediator for retinoic acid and thyroid receptors, but substantially lacking the ability to activate steroid/thyroid hormone receptor activity.

The addition of invention co-suppressor is optional in the above-described assay because it is present endogenously in most host cells employed for such assays. It is preferred, to ensure the presence of a fairly constant amount of co-suppressor, and to ensure that co-suppressor is not a limiting reagent, that co-suppressor be supplied exogenously to the above-described assays.

Mutant receptors contemplated for use in the practice of the present invention are conveniently produced by expression plasmids, introduced into the host cell by transfection. Mutant receptors contemplated for use herein include RAR403 homodimers, RAR403-containing heterodimers, TR160 homodimers, TR160-containing heterodimers, and the like.

Reporter constructs contemplated for use in the practice of the present invention comprise:
(a) a promoter that is operable in the host cell,
(b) a hormone response element, and
(c) a DNA segment encoding a reporter protein,
wherein the reporter protein-encoding DNA segment is operatively linked to the promoter for transcription of the DNA segment, and
wherein the hormone response element is operatively linked to the promoter for activation thereof.

Hormone response elements contemplated for use in the practice of the present invention are well known in the art, as has been noted previously.

Exemplary reporter genes include chloramphenicol transferase (CAT), luciferase (LUC), beta-galactosidase (β-gal), and the like. Exemplary promoters include the simian virus (SV) promoter or modified form thereof (e.g., ΔSV), the thymidine kinase (TK) promoter, the mammary tumor virus (MTV) promoter or modified form thereof (e.g., ΔMTV), and the like [see, for example, Mangelsdorf et al., in Nature 345:224-229 (1990), Mangelsdorf et al., in Cell 66:555-561 (1991), and Berger et al., in J. Steroid Biochem. Molec. Biol. 41:733-738 (1992)].

As used herein in the phrase "operative response element functionally linked to an operative reporter gene", the word "operative" means that the respective DNA sequences (represented by the terms "GAL4 response element" and "reporter gene") are operational, i.e., work for their intended purposes; the word "functionally" means that after the two segments are linked, upon appropriate activation by a ligand-receptor complex, the reporter gene will be expressed as the result of the fact that the "GAL4 response element" was "turned on" or otherwise activated.

In practicing the above-described functional bioassay, the expression plasmid and the reporter plasmid are co-transfected into suitable host cells. The transfected host cells are then cultured in the presence and absence of a test compound to determine if the test compound is able to produce activation of the promoter operatively linked to the response element of the reporter plasmid. Thereafter, the transfected and cultured host cells are monitored for induction (i.e., the presence) of the product of the reporter gene sequence.

Any cell line can be used as a suitable "host" for the functional bioassay contemplated for use in the practice of the present invention. Thus, cells contemplated for use in the practice of the present invention include transformed cells, non-transformed cells, neoplastic cells, primary cultures of different cell types, and the like. Exemplary cells which can be employed in the practice of the present invention include Schneider cells, CV-1 cells, HuTu80 cells, F9 cells, NTERA2 cells, NB4 cells, HL-60 cells, 293 cells, Hela cells, yeast cells, and the like. Preferred host cells for use in the functional bioassay system are COS cells and CV-1 cells. COS-1 (referred to as COS) cells are monkey kidney cells that express SV40 T antigen (Tag); while CV-1 cells do not express SV40 Tag. The presence of Tag in the COS-1 derivative lines allows the introduced expression plasmid to replicate and provides a relative increase in the amount of receptor produced during the assay period. CV-1 cells are presently preferred because they are particularly convenient for gene transfer studies and provide a sensitive and well-described host cell system.

The above-described cells (or fractions thereof) are maintained under physiological conditions when contacted with physiologically active compound. "Physiological conditions" are readily understood by those of skill in the art to comprise an isotonic, aqueous nutrient medium at a temperature of about 37° C.

In accordance with yet another aspect of the present invention, there is provided a method to identify compounds which activate steroid/thyroid hormone receptor activity, but substantially lack the ability to relieve the suppression caused by a co-suppressor as described hereinabove, said method comprising:

comparing the reporter signal produced by two different expression systems in the absence and presence of test compound,
wherein said first expression system comprises a complex comprising:
a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer, or retinoic acid receptor-retinoid X receptor heterodimer,
a response element for said member of the steroid/thyroid hormone superfamily of receptors, wherein said response element is operatively linked to a reporter, and
optionally, invention co-suppressor, and
wherein said second expression system comprises a complex comprising:
a homodimeric or heterodimeric form of the same member of the steroid/thyroid hormone superfamily of receptors as employed in said first expression system, wherein said member is mutated such that it retains hormone dependent activation activity but has lost its ability to repress basal level promoter activity of target genes,
the same response element-reporter combination as employed in said first expression system, and
optionally, invention co-suppressor, and thereafter
selecting those compounds which provide:
a higher reporter signal upon exposure of said compound to said second expression system, relative to reporter signal in the absence of compound, and
substantially the same reporter signal upon exposure of said compound to said first expression system, relative to reporter signal in the absence of said compound,
wherein said selected compounds are capable of activating steroid/thyroid hormone receptor activity, but substantially lacking the ability to relieve the suppression caused by a co-suppressor having a structure and function characteristic of the silencing mediator for retinoic acid and thyroid receptors.

In accordance with a still further aspect of the present invention, there is provided a method to identify compounds which relieve the suppression of steroid/thyroid hormone receptor activity caused by a co-suppressor as described hereinabove, and activate said receptor, said method comprising:

comparing the reporter signal produced by two different expression systems in the absence and presence of test compound,
wherein said first expression system comprises a complex comprising:
a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer, or retinoic acid receptor-retinoid X receptor heterodimer,
a response element for said member of the steroid/thyroid hormone superfamily of receptors, wherein said response element is operatively linked to a reporter, and
optionally, invention co-suppressor, and
wherein said second expression system comprises a complex comprising:
a homodimeric or heterodimeric form of the same member of the steroid/thyroid hormone superfamily of receptors as employed in said first expression system, wherein said member is mutated such that it retains hormone dependent activation activity but has lost its ability to repress basal level promoter activity of target genes,
the same response element-reporter combination as employed in said first expression system, and
optionally, invention co-suppressor, and thereafter selecting those compounds which provide:
increased reporter signal upon exposure of said compound to said second expression system, relative to reporter signal in the absence of said compound, and
substantially increased reporter signal upon exposure of said compound to said first expression system, relative to reporter signal in the absence of said compound,
wherein said selected compounds are capable of relieving the suppression of steroid/thyroid hormone receptor activity caused by a co-suppressor having a structure and function characteristic of the silencing mediator for retinoic acid and thyroid receptors, and activating said receptor.

In accordance with still another embodiment of the present invention, there are provided modified forms of the above-described co-suppressor, including:
full length silencing mediator for retinoic acid and thyroid receptors plus GAL4 DNA binding domain,
full length silencing mediator for retinoic acid and thyroid receptors plus GAL4 activation domain,
full length silencing mediator for retinoic acid and thyroid receptors plus glutathione S-transferase (GST) tag,
and the like.

The above-described modified forms of invention co-suppressor can be used in a variety of ways, e.g., in the assays described herein.

An especially preferred modified co-suppressor of the invention comprises full length silencing mediator for retinoic acid and thyroid receptors plus GAL4 activation domain.

In accordance with a still further embodiment of the present invention, there is provided a method to identify compounds which disrupt the ability of a co-suppressor as described hereinabove to complex with steroid/thyroid hormone receptors, without substantially activating said receptor, said method comprising:
comparing the reporter signal produced by two different expression systems in the absence and presence of test compound,
wherein said first expression system comprises a complex comprising:
a modified co-suppressor as described above,
a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer or retinoic acid receptor-retinoid X receptor heterodimer, and
a response element for said member of the steroid/thyroid hormone superfamily of receptors, wherein said response element is operatively linked to a reporter, and
wherein said second expression system comprises a complex comprising:
said modified co-suppressor,
a homodimeric or heterodimeric form of the same member of the steroid/thyroid hormone superfamily of receptors as employed in said first expression system, wherein said member is mutated such that it retains hormone dependent activation activity but has lost its ability to repress basal level promoter activity of target genes, and
the same response element-reporter combination as employed in said first expression system, and thereafter
selecting those compounds which provide:
a lower reporter signal upon exposure of said compound to said first expression system, relative to reporter signal in the absence of said compound, and
substantially the same reporter signal upon exposure of said compound to said second expression system, relative to reporter signal in the absence of said compound,
wherein said selected compounds are capable of disrupting the ability of a co-suppressor having a structure and function characteristic of the silencing mediator for retinoic acid and thyroid receptors to complex with steroid/thyroid hormone receptors, without substantially activating said receptor.

Mutant receptors contemplated for use in this embodiment of the present invention include RAR403 homodimers, RAR403-containing heterodimers, TR160 homodimers, TR160-containing heterodimers, and the like.

Suitable host cells for use in this embodiment of the present invention include mammalian cells as well as yeast cells. Yeast cells are presently preferred because they introduce no background since SMRT (i.e., silencing mediator (co-repressor) for retinoic acid receptor (RAR) and thyroid hormone receptor (TR)) is not endogenous to yeast.

In accordance with yet another embodiment of the present invention, there is provided a method to identify compounds which activate steroid/thyroid hormone receptor activity, but substantially lack the ability to disrupt a complex comprising a steroid/thyroid hormone receptor and a co-suppressor as described hereinabove, said method comprising:
comparing the reporter signal produced by two different expression systems in the absence and presence of test compound,
wherein said first expression system comprises a complex comprising:
a modified co-suppressor as described above,
a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer or retinoic acid receptor-retinoid X receptor heterodimer, and
a response element for said member of the steroid/thyroid hormone superfamily of receptors, wherein said response element is operatively linked to a reporter, and
wherein said second receptor system comprises:
said modified co-suppressor,
a homodimeric or heterodimeric form of the same member of the steroid/thyroid hormone superfamily of receptors as employed in said first expression system, wherein said member is mutated such that it retains hormone dependent activation activity but has lost its ability to repress basal level promoter activity of target genes, and
the same response element-reporter combination as employed in said first expression system, and thereafter
selecting those compounds which provide:
a higher reporter signal upon exposure of said compound to said second expression system, relative to reporter signal in the absence of compound, and
substantially the same reporter signal upon exposure of said compound to said first expression system, relative to reporter signal in the absence of compound, wherein said selected compounds are capable of activating steroid/thyroid hormone receptor activity, but substantially lack the ability to disrupt the complex of a co-suppressor having a structure and function characteristic of the silencing mediator for retinoic acid and thyroid receptors and a steroid/thyroid hormone receptor.

Suitable host cells for use in this embodiment of the present invention include mammalian cells as well as yeast cells. Yeast cells are presently preferred because they introduce no background since SMRT is not endogenous to yeast.

In accordance with a still further embodiment of the present invention, there is provided a method to identify compounds which activate a steroid/thyroid hormone receptor, and disrupt the ability of a co-suppressor as described hereinabove to complex with said receptor, said method comprising:

comparing the reporter signal produced by two different expression systems in the absence and presence of test compound,
wherein said first expression system comprises a complex comprising:
a modified co-suppressor as described above,
a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer or retinoic acid receptor-retinoid X receptor heterodimer, and
a response element for said member of the steroid/thyroid hormone superfamily of receptors, wherein said response element is operatively linked to a reporter, and
wherein said second expression system comprises a complex comprising:
said modified co-suppressor,
the same homodimeric or heterodimeric member of the steroid/thyroid hormone superfamily of receptors as employed in said first expression system, wherein said member is mutated such that it retains hormone dependent activation activity but has lost its ability to repress basal level promoter activity of target genes, and
the same response element-reporter combination as employed in said first expression system, and thereafter
selecting those compounds which provide:
a reduction in reporter signal upon exposure of compound to said first expression system, relative to reporter signal in the absence of said compound, and increased reporter signal upon exposure of compound to said second expression system, relative to reporter signal in the absence of said compound,
wherein said selected compounds are capable of activating a steroid/thyroid hormone receptor and disrupting a complex comprising steroid/thyroid hormone receptor and a co-suppressor having a structure and function characteristic of the silencing mediator for retinoic acid and thyroid receptors.

Suitable host cells for use in this embodiment of the present invention include mammalian cells as well as yeast cells. Yeast cells are presently preferred because they introduce no background since SMRT is not endogenous to yeast.

In accordance with yet another aspect of the present invention, there is provided a method to identify compounds which activate a steroid/thyroid hormone receptor and/or disrupt the ability of a co-suppressor as described hereinabove to complex with said receptor, said method comprising:

comparing the reporter signals produced by a combination expression system in the absence and presence of test compound,
wherein said combination expression system comprises:
a first homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer, or retinoic acid receptor-retinoid X receptor heterodimer,
a second homodimeric or heterodimeric form of the same member of the steroid/thyroid hormone superfamily of receptors as employed in said first homodimer or heterodimer, wherein said member is mutated such that it retains hormone dependent activation activity but has lost its ability to repress basal level promoter activity of target genes (i.e., provides basal level expression),
wherein either said first homodimer (or heterodimer) or said second homodimer (or heterodimer) is operatively linked to a GAL4 DNA binding domain,
a response element for said member of the steroid/thyroid hormone superfamily of receptors, wherein said response element is operatively linked to a first reporter,
a GAL4 response element, wherein said response element is operatively linked to a second reporter, and
optionally a co-suppressor of steroid/thyroid hormone receptor activity, said co-suppressor having a structure and function characteristic of the silencing mediator for retinoic acid and thyroid receptors, and thereafter
identifying as capable of relieving the suppression of steroid/thyroid hormone receptor activity caused by a co-suppressor having a structure and function characteristic of the silencing mediator for retinoic acid and thyroid receptors, but substantially lacking the ability to activate steroid/thyroid hormone receptor activity those compounds which provide:
a higher reporter signal from the reporter responsive to the first member upon exposure of said compound to said first member, relative to reporter signal in the absence of said compound, and
substantially the same reporter signal from the reporter responsive to the second member upon exposure of said compound to said second member, relative to reporter signal in the absence of said compound, or
identifying as capable of activating steroid/thyroid hormone receptor activity, but substantially lacking the ability to relieve the suppression caused by a co-suppressor having a structure and function characteristic of the silencing mediator for retinoic acid and thyroid receptors those compounds which provide:
a higher reporter signal from the reporter responsive to the second member upon exposure of said compound to said second member, relative to reporter signal in the absence of compound, and
substantially the same reporter signal from the reporter responsive to the first member upon exposure of said compound to said first member, relative to reporter signal in the absence of said compound, or identifying as capable of relieving the suppression of steroid/thyroid hormone receptor activity caused by a co-suppressor having a structure and function characteristic of the silencing mediator for retinoic acid and thyroid receptors, and activating said receptor those compounds which provide:

a higher reporter signal from the reporter responsive to the second member upon exposure of said compound to said second member, relative to reporter signal in the absence of said compound, and a greater increase in reporter signal from the reporter responsive to the first member upon exposure of said compound to said first member, relative to reporter signal in the absence of said compound.

Thus, the change in expression level of the two different reporters introduced in a single transfection can be monitored simultaneously. Based on the results of this single transfection, one can readily identify the mode of interaction of test compound with the receptor/SMRT complex.

Exemplary GAL4 response elements are those containing the palindromic 17-mer:

5'-CGGAGGACTGTCCTCCG-3' (SEQ ID NO:3), such as, for example, 17MX, as described by Webster et al., in Cell 52:169-178 (1988), as well as derivatives thereof. Additional examples of suitable response elements include those described by Hollenberg and Evans in Cell 55:899-906 (1988); or Webster et al. in Cell 54:199-207 (1988).

In accordance with still another embodiment of the present invention, there is provided a method to identify compounds which activate a steroid/thyroid hormone receptor and/or disrupt the ability of a co-suppressor as described hereinabove to complex with said receptor, said method comprising:

comparing the reporter signals produced by a combination expression system in the absence and presence of test compound, wherein said combination expression system comprises:

a modified co-suppressor as described above, a first homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer, or retinoic acid receptor-retinoid X receptor heterodimer, a second homodimeric or heterodimeric form of the same member of the steroid/thyroid hormone superfamily of receptors as employed in said first homodimer or heterodimer, wherein said member is mutated such that it retains hormone dependent activation activity but has lost its ability to repress basal level promoter activity of target genes, wherein either said first homodimer (or heterodimer) or said second homodimer (or heterodimer) is operatively linked to a GAL4 DNA binding domain, a response element for said member of the steroid/thyroid hormone superfamily of receptors, wherein said response element is operatively linked to a first reporter, a GAL4 response element, wherein said response element is operatively linked to a second reporter, and thereafter identifying as capable of disrupting the ability of a co-suppressor having a structure and function characteristic of the silencing mediator for retinoic acid and thyroid receptors to complex with a steroid/thyroid hormone receptor, without substantially activating steroid/thyroid hormone receptor, those compounds which provide:

a lower reporter signal from the reporter responsive to the first member upon exposure of said compound to said first member, relative to reporter signal in the absence of said compound, and substantially the same reporter signal from the reporter responsive to the second member upon exposure of said compound to said second member, relative to reporter signal in the absence of said compound, or identifying as capable of activating steroid/thyroid hormone receptor activity, but substantially lacking the ability to disrupt a complex comprising a steroid/thyroid hormone receptor and a co-suppressor having a structure and function characteristic of the silencing mediator for retinoic acid and thyroid receptors, those compounds which provide:

a higher reporter signal from the reporter responsive to the second member upon exposure of said compound to said second member, relative to reporter signal in the absence of compound, and substantially the same reporter signal from the reporter responsive to the first member upon exposure of said compound to said first member, relative to reporter signal in the absence of said compound, or identifying as capable of disrupting a complex comprising a steroid/thyroid hormone receptor and a co-suppressor having a structure and function characteristic of the silencing mediator for retinoic acid and thyroid receptors, and activating said receptor those compounds which provide:

a reduction in reporter signal from the reporter responsive to the first member upon exposure of said compound to said first member, relative to reporter signal in the absence of said compound, and increased reporter signal from the reporter responsive to the second member upon exposure of said compound to said second member, relative to reporter signal in the absence of said compound.

In accordance with a still further aspect of the present invention, there is provided a method to identify compounds which relieve the suppression of steroid/thyroid hormone receptor activity caused by a co-suppressor as described hereinabove, said method comprising determining the effect of adding test compound to an expression system comprising:

a modified member of the steroid/thyroid hormone superfamily of receptors, wherein said modified member contains an activation domain which renders said receptor constitutively active, a fusion protein comprising the receptor interaction domain of SMRT operatively linked to the GAL4 DNA binding domain, and a GAL4 response element operatively linked to a reporter.

Prior to addition of an effective ligand for the member of the steroid/thyroid hormone superfamily of receptors employed herein, the association of the modified member and the fusion protein will be effective to bind the GAL4 response element and activate transcription of the reporter. The presence of an effective ligand is indicated by a reduction of reporter signal upon exposure to ligand, which disrupts the interaction of the modified member and fusion protein.

Activation domains contemplated for use in the practice of the present invention are well known in the art and can readily be identified by the artisan. Examples include the GAL4 activation domain, BP64, and the like.

To summarize, a novel nuclear receptor co-repressor which mediates the transcriptional silencing of RAR and TR has been identified. This discovery is of great interest because transcriptional silencing has been shown to play an important role in development, cell differentiation and the oncogenic activity of v-erbA (Baniahmad et al., *EMBO J.* 11:1015-1023 (1992)); Gandrillon et al., *Cell* 49:687-697 (1989)); Zenke et al., *Cell* 61:1035-1049 (1990); Barlow et al., *EMBO J.* 13:4241-4250 (1994); Levine and Manley, *Cell* 59:405-408 (1989); Baniahmad et al., *Proc. Natl. Acad. Sci. USA* 89:10633-10637 (1992b) and Saitou et al., *Nature* 374:159-162 (1995)). In fact, v-erbA mutants that harbor the Pro160–>Arg change in the TR neither suppress basal transcription nor are capable of oncogenic transformation (Damm and Evans, (1993) supra)

The function of SMRT as a silencing mediator (co-repressor) of RAR and TR is analogous to mSin3 in the Mad-Max-Sin3 ternary complex (Schreiber-Agus et al., *Cell* 80:777-786 (1995); and Ayer et al., *Cell* 80:767-776 (1995)). Because GAL-SMRT functions as a potent repressor when bound to DNA, it is reasonable to speculate that the function of the unliganded receptors is to bring with them SMRT to the template via protein-protein interaction. Thus, the repressor function is intrinsic to SMRT as opposed to the TR or RAR itself (Baniahmad et al., *Proc. Natl. Acad. Sci. USA* 90:8832-8836 (1993); and Fondell et al., *Genes Dev* 7:1400-1410 (1993)). It is demonstrated herein that the ligand triggers a dissociation of SMRT from the receptor, which would lead to an initial step in the activation process. This would be followed (or be coincident) with an induced conformational change in the carboxy-terminal transactivation domain (τc, also called AF-2), allowing association with co-activators on the transcription machinery (Douarin et al., *EMBO J.* 14:2020-2033 (1995); Halachmi et al., *Science* 264:1455-1458 (1994); Lee et al., *Nature* 374:91-94 (1995); and Cavailles et al., *Proc. Natl. Acad. Sci. USA* 91:10009-10013 (1994)). Thus, as has previously been suggested (Damm and Evans (1993) supra), the ligand dependent activation of TR would represent two separable processes including relief of repression and net activation. The isolation of SMRT now provides a basis for dissecting the molecular basis of trans-repression.

The invention will now be described in greater detail by reference to the following non-limiting examples.

EXAMPLE 1

Isolation of SMRT

Using a GAL4 DBD-RXR fusion protein (see, for example, U.S. Ser. No. 08/177,740, incorporated by reference herein in its entirety) as a bait in a yeast two-hybrid screening system (Durfee et al. *Genes Dev* 7:555-569 (1993)), several cDNA clones encoding receptor interacting proteins were isolated. One of these proteins, SMRT, inter- acts strongly with unliganded RAR and TR but only weakly with RXR or other receptors in yeast. This protein was selected for further characterization.

EXAMPLE 2

Far-western Blotting Procedure

Total bacteria extracts expressing GST fusions of hRARα (aa 156-462) or hRXRα LBD (aa 228-462) and control extracts expressing GST alone or GST-PML fusion protein were subjected to SDS/PAGE and electroblotted onto nitrocellulose in transfer buffer (25 mM Tris, pH 8.3/192 mM glycine/0.01% SDS). After denaturation/renaturation from 6 M to 0.187 M guanidine hydrochloride in HB buffer (25 mM Hepes, pH 7.7/25 mM NaCl/5 mM $MgCl_2$/1 mM DTT) filters were saturated at 4° C. in blocking buffer (5% milk, then 1% milk in HB buffer plus 0.05% NONIDET® P-40 (nonylphenol polyoxyethylene ether)). In vitro translated $^{35}$S-labeled proteins were diluted into H buffer (20 mM Hepes, pH 7.7/75 mM KCl/0.1 mM EDTA/2.5 mM $MgCl_2$/ 0.05% NONIDET® P-40 (nonylphenol polyoxyethylene ether)/1% milk/1 mM DTT) and the filters were hybridized overnight at 4° C. with (1 μM) or without ligand. After three washes with H buffer, filters were dried and exposed for autoradiography or quantitated by phosphoimager.

GST-SMRT is a GST fusion of the C-SMRT encoded by the yeast two hybrid clone. GST-SMRT has been purified, but contains several degradation products.

For yeast two-hybrid screening, a construct expressing the GAL4 DBD-hRXRα LBD (aa 198-462) fusion protein was used to screen a human lymphocyte cDNA library as described (Durfee et al., (1993) supra). Full length SMRT cDNA was isolated from a human HeLa cDNA library (Clontech) using the two-hybrid insert as a probe.

Using the above-described far-western blotting procedure, $^{35}$S-labeled SMRT preferentially complexes with bacterial extracts expressing the RAR, marginally associates with RXR and shows no association with control extracts. In contrast, $^{35}$S-PPAR selectively associates with its heterodimeric partner, RXR, but not with RAR. In a similar assay, $^{35}$S-labeled RAR or TR interacts strongly with SMRT and their heterodimeric partner, RXR, but not with degraded GST products, while $^{35}$S-RXR interacts only weakly with SMRT. Binding of ligand to RAR or TR reduces their interactions with SMRT but not with RXR, while binding of ligand to RXR has only slight effect. FIG. 1 shows the quantitation of a dose-dependent dissociation of SMRT from RAR or TR by all-trans retinoic acid (atRA) or thyroid hormone (triiodothyronine or T3), demonstrating that the amount of ligand required for 50% dissociation in both cases are close to the kds for both ligands (Munoz et al. *EMBO J.* 7:155-159 (1988); Sap et al., *Nature* 340:242-244 (1989); and Yang et al., *Proc. Natl. Acad. Sci. USA* 88:3559-3563 (1991)).

Full length SMRT encodes a polypeptide of 1495 amino acids rich in proline and serine residues (see FIG. 2 and SEQ ID NO:1). Genbank database comparison reveals similarity of the C-terminal domain of SMRT to a partial cDNA encoding another receptor interacting protein, RIP13 (Seol et al., (1995) supra), whose role in receptor signaling is unknown. Within this region, there can be identified several potential heptad repeats which might mediate protein-protein interaction with the "a-helical sandwich" structure (Bourguet et al., *Nature* 375:377-382 (1995)) of the ligand binding domain (LBD) of receptors.

EXAMPLE 3

Characterization of SMRT

Unlike other nuclear receptors, unliganded RAR and TR possess a strong silencing domain which represses basal level promoter activity of their target genes (Damm et al., *Nature* 339:593-597 (1989); Brent et al., *New Biol.* 1:329-336 (1989); Baniahmad et al., *Cel* 61:505-514 (1990); and Baniahmad et al., *EMBO J.* 11:1015-1023 (1992)). The preferential interaction of SMRT with RAR and TR in the absence of hormone suggests that SMRT may play a role in mediating the transcriptional silencing effect of the receptor.

To further investigate the involvement of SMRT in silencing, the interaction of SMRT with mutant receptors which display distinct silencing and/or transactivation activities was tested as follows. $^{35}$S-methionine labeled receptors were used as probes to hybridize immobilized GST-SMRT in the presence (10 μM) or absence of all-trans retinoic acid (atRA). The total bacteria extract expressing GST-RXR was included as a control.

When quantitated by phosphoimager, RAR403 shows a 4-fold better interaction with SMRT than wild type RAR. Both full length RAR or a deletion mutant expressing only the ligand binding domain (LBD, referred to as ΔΔR) associate with SMRT; this association is blocked by ligand.

These results confirm that the LBD alone is sufficient in the interaction. The carboxy-terminal deletion mutant RAR403 is a potent dominant negative suppressor of basal level promoter activity of RAR target genes (Damm et al., *Proc. Natl. Acad. Sci. USA* 90:2989-2993 (1993); Tsai and Collins, *Proc. Natl. Acad. Sci. USA* 90:7153-7157 (1993); and Tsai et al., *Genes Dev* 6:2258-2269 (1992)). As might be predicted from the above studies, RAR403 and its amino terminal deletion derivative, ΔΔR403, interact strongly with SMRT in either the presence or absence of ligand, consistent with SMRT mediating the repressor activity of this mutant.

EXAMPLE 4

Interaction of SMRT with TR Mutants

The interaction of SMRT with two different classes of TR mutants was analyzed next. The first mutant employed is the naturally occurring oncogene, v-erbA, which has strong silencing ability but no transactivation activity (Sap et al., (1989) supra Sap et al., *Nature* 324:635-640 (1986); Weinberger et al., *Nature* 318:670-672 (1985); and Weinberger et al., *Nature* 324:641-646 (1986)). The second mutant employed is a single amino acid change (Pro 160–>Arg) of the rTRa (TR160) which has previously been shown to lose its capacity in basal level suppression but retains hormone dependent transactivation (Thompson et al., *Science* 237: 1610-1614 (1987); and Damm and Evans, *Proc. Natl. Acad. Sd. USA* 90:10668-10672 (1993)). If SMRT is involved in silencing, it would be expected that SMRT should interact with the v-erbA, but show little or no association with the silencing-defective TR160 mutant.

Interaction of the oncogenic v-erbA and rTRα R160 mutant (TR160) with GST-SMRT was determined in a far-western assay as described above (see Example 2). When quantitated by phosphoimager, the v-erbA shows an 18-fold better interaction with SMRT than hTRβ, and the TR160 mutant shows a 10-fold lower signal than the rTRα.

As one might expect, v-erbA interacts strongly with SMRT both in presence or absence of ligand. In contrast, full length TR160 mutant or LBD of TR160 ΔΔTR160) does not interact significantly with SMRT when compared to the wild type receptor.

These data demonstrate that SMRT plays an important role in mediating transcriptional silencing effects of both RAR and TR. These data also suggest that the release of SMRT from receptors could be a prerequisite step in ligand-dependent transactivation by nuclear receptors.

EXAMPLE 5

Formation of Ternary Complexes Containing SMRT

RAR and TR form heterodimers with RXR, resulting in a complex with high DNA binding ability (Bugge et al., *EMBO J.* 11:1409-1418 (1992); Yu et al., *Cell* 67:1251-1266 (1991); and Kliewer et al., *Nature* 355:446-449 (1992)). Since SMRT interacts with RAR and TR, tests were conducted to determine whether SMRT can also interact with the receptor-DNA complex. Thus, the interaction of SMRT with RXR-RAR heterodimer on a DR5 element (i.e., an AGGTCA direct repeat spaced by five nucleotides) was determined in a gel retardation assay, which is carried out as follows. In vitro translated receptor or unprogrammed reticulocyte lysate (URL) was incubated with 1 μg of poly dIdC on ice for 15 minutes in a total volume of 20 μl containing 75 mM KCl, 7.5% glycerol, 20 mM Hepes (pH 7.5), 2 mM DTT and 0.1% NONIDET® P-40 (nonylphenol polyoxyethylene ether), with or without ligand (in the range of about 10-100 nM employed). A $^{32}$P labeled, double stranded oligonucleotide probe was added into the binding reaction (10,000 cpm per reaction), and the reaction was further incubated for 20 minutes at room temperature. The protein-DNA complex was separated on a 5% native polyacrylamide gel at 150 volts.

SMRT is seen to form a ternary complex with the RXR-RAR heterodimer on a DNA response element in the gel retardation assay. Addition of ligand releases SMRT from this complex in a dose-dependent manner.

Similarly, SMRT is seen to form a ternary complex with the RXR-TR heterodimer on a TR response element; addition of T3 disrupts the formation of this complex.

These data demonstrate that SMRT can be recruited to DNA response elements via protein-protein interaction with RAR or TR in the absence of hormone. Binding of hormone disrupts receptor-SMRT interaction and releases SMRT from the receptor-DNA complex.

EXAMPLE 6

Transient Transfection Assay

CV-1 cells were plated in 24 well plates at a density of 50,000 cells per well. Expression plasmids were transfected into cells by lipofection using DOTAP. In each transfection, 5 ng of GAL-RAR and 15 ng of v-erbA or SMRT were used together with 150 ng of reporter construct containing 4 copies of GAL4 binding sites in front of a minimal thymidine kinase promoter and a CMX-β-gal construct as an internal control. The relative luciferase activity was calculated by normalizing to the β-gal activity.

EXAMPLE 7

Reversal of Transcriptional Silencing

Recently, it has been shown that over expression of RAR or TR could reverse the transcriptional silencing effect of the GAL4 DBD fusion of TR (GAL-TR) or RAR (GAL-RAR) (Baniahmad et al., *Mol Cell Biol* 15:76-86 (1995); and Casanova et al., *Mol Cell Biol.* 14:5756-5765 (1994)), co-repressor. A similar effect is observed herein when over expression of v-erbA or RAR403 mutants are shown to reverse the silencing effect of GAL-RAR and GAL-TR on the basal activity of a luciferase reporter (see FIGS. 3A and 3B).

Figure 3:
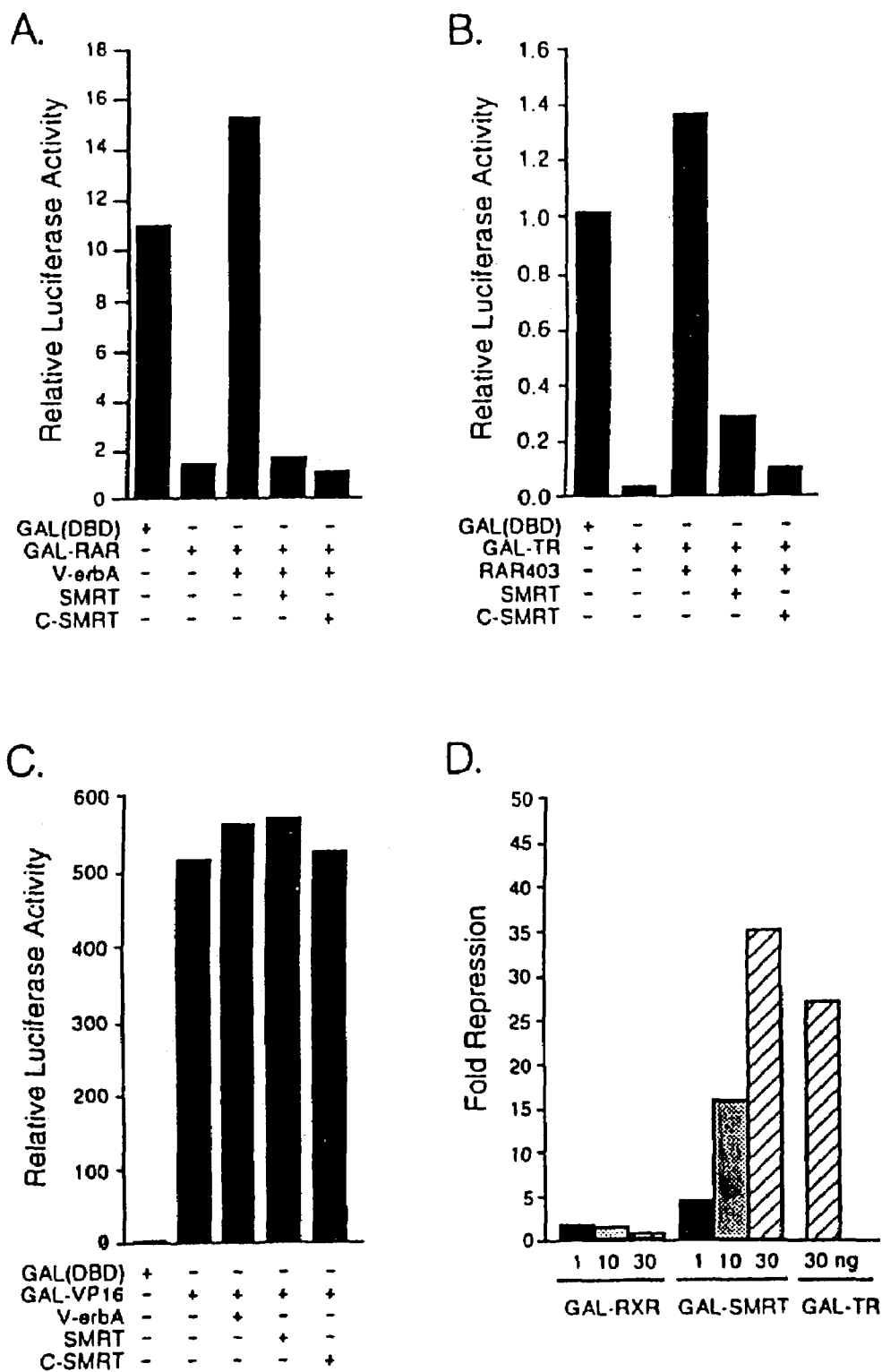
FIG. 3 collectively illustrates mediation of the silencing effect of hRARCα and hTRβ by SMRT in vivo.

In principle, over expression of SMRT should restore repressor activity when co-expressed with v-erbA or RAR403 competitors. Indeed, results presented in FIG. 3C show that both the full length and the C-terminal domain of SMRT (C-SMRT) can titrate out v-erbA or RAR403 competitor activity and re-endow GAL-RAR and GAL-TR with silencing activity. In contrast, neither v-erbA nor SMRT show any effect on the transactivation activity of GAL-VP16 fusion. Thus, SMRT is able to block the titration effect of v-erbA and RAR403 and functionally replaces the putative co-repressor in this system.

EXAMPLE 8

Direct Recruitment of SMRT to a Heterologous Promoter

If SMRT is the mediator of transcription silencing of TR and RAR by interaction with template-bound unliganded receptors, then direct recruitment of SMRT to a heterologous promoter should result in repression of basal level activity. This was tested by fusing full length SMRT to the GAL4 DBD (GAL-SMRT). The effect of the resulting fusion protein on the activity of the thymidine kinase promoter containing four GAL4 binding sites was analyzed. FIG. 3D shows that GAL-SMRT, like GAL-TR, can silence basal promoter activity in a dose-dependent manner. In contrast, GAL-RXR shows no suppression.

These data suggest that SMRT, when recruited to a promoter by direct DNA binding or via association with an unliganded receptor, functions as a potent transcriptional repressor.

While the invention has been described in detail with reference to certain preferred embodiments thereof, it will be understood that modifications and variations are within the spirit and scope of that which is described and claimed.

SEQUENCE ID NO:1

```
   1  MEAWDAH(P)DKEAFAAEAQKL(P)GD(P)(P)CWTSGL(P)F(P)V(P)(P)REVIKAS(P)HA(P)D(P)

51  SAFSYA(P)(P)GH(P)L(P)LGLHDTAR(P)VL(P)R(P)(P)TISN(P)(P)(P)LISSAKH(P)SVLERQI

101  GAISQGMSVQLHV(P)YSEHAKA(P)VQ(P)VTMGL(P)L(P)MD(P)KKLA(P)FSGVKQEQL

151  SPRGQAGPPESLGVPTAQEASVLRGTALGSVPGGSITKGIPSTRVPSDSA

201  ITYRGSITHGTPADVLYKGTITRIIGEDSPSRLDRGREDSLPKGHVIYEG

251  KKGHVLSYEGGMSVTQCSKEDGRSSSGPPHETAAPKRTYDMMEGRVGRAI

301  SSASIEGLMGRAIPPERHSPHHLKEQHHIRGSITQGIPRSYVEAQEDYLR

351  REAKLLKREGTPPPPPPSRDLTEAYKTQALGPLKLKPAHEGLVATVKEAG

401  RSIHEIPREELRHTPELPLAPRPLKEGSITQGTPLKYDTGASTTGSKKHD

451  VRSLIGSPGRTFPPVHPLDVMADARALERACYEESLKSRPGTASSSGGSI

501  ARGAPVIVPELGKPRQSPLTYEDHGAPFAGHLPRGSPVTMREPTPRLQEG

551  SLSSSKASQDRKLTSTPREIAKSPHSTVPEHHPHPISPYEHLLRGVSGVD

601  LYRSHIPLAFDPTSIPRGIPLDAAAAYYLPRHLAPNPTYPHLYPPYLIRG

651  YPDTAALENRQTIINDYITSQQMHHNTATAMAQRADMLRGLSPRESSLAL

701  NYAAGPRGIIDLSQVPHLPVLVPPTPGTPATAMDRLAYLPTAPQPFSSRH

751  SSSPLSPGGPTHLTKPTTTSSSERERDRDRERDRDREREKSILTSTTTVE

801  HAPIWRPGTEQSSGSSGSSGGGGSSSRPASHSHAHQHSPISPRTQDALQ

851  QRPSVLHNTGMKGIITAVEPSKPTVLRSTSTSSPVRPAATFPPATHCPLG

901  GTLDGVYPTLMEPVLLPKEAPRVARPERPRADTGHAFLAKPPARSGLEPA

|→C-SMRT
 951  SSPSKGSEPRPLVPPVSGHATIARTPAKNLAPHHASPDPPAPPASASDPH

1001  REKTQSKPFSIQELELRSLGYHGSSYSPEGVEPVSPVSSPSLTHDKGLPK

1051  HLEELDKSHLEGELRPKQPGPVKLGGEAAHLPHLRPLPES(Q)PSSSPLL(Q)T
```

-continued

```
1101  APGVKGH Q RVVTLA Q HISEVIT Q DYTRHHP Q Q LSAPLPAPLYSFPGASCP
1151  VLDLRRPPSDLYLPPPDHGAPARGSPHSEGGKRSPEPNKTSVLGGGEDGI
1201  EPVSPPEGMTEPGHSRSAVYPLLYRDGEQTEPSRMGSKSPGNTSQPPAFF
1251  SK I TESNSA H V KSKKQE I NKKLNT H NRNEPEYNISQPGTEIFNMPAITGT
1301  GL H TYRSQA V QEHASTNMGLEAIIRKALM[GKYDQW.EESPPLSANAFNPL
1350  NASASLPAAMPITAADGRSDHTLTSP].GGGGKAKVSGRPSSRKAKSPAPG
1399  LA..SGDRPPSVSSVHSEGDCNRRTPLTNRVWEDRPSSAGSTPFPYNPL I
1447  MRLQAG V MASPPPPG I PAGSGP I ..AGPHHA...WDEEPKPL I CSQYET I
1492  SDSE*  1495
```

SEQUENCE ID NO:2

GKYDQWEESPPLSANAFNPLNASASLPAAMPITAADGRSDHTLTSP

---

That which is claimed is:

1. A method to identify compounds which relieve the suppression of steroid/thyroid hormone receptor activity caused by a co-suppressor having a structure and function characteristic of a silencing mediator for retinoic acid and thyroid hormone receptors, thereby activating said receptor, said method comprising:

determining the effect of a test compound on a reporter signal produced by a first expression system and on a reporter signal produced by a second expression system, wherein said first expression system comprises a complex comprising:

a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer, or retinoic acid receptor-retinoid X receptor heterodimer, a response element for said member of the steroid/thyroid hormone superfamily of receptors, wherein said response element is operatively linked to a reporter, and said co-suppressor, wherein said co-suppressor comprises amino acid residues 1-1329 plus 1376-1495, as set forth in SEQ ID NO:1, or conservative amino acid variations thereof and, wherein said co-suppressor forms a complex with at least one member of the steroi~Jthyroid hormone superfamily of receptors and wherein said second expression system comprises a complex comprising:

a homodimeric or heterodimeric form of the same member of the steroid/thyroid hormone superfamily of receptors as employed in said first expression system, wherein said member is mutated such that it retains hormone dependent activation activity but has lost its ability to repress basal level promoter activity of target genes, the same response element-reporter combination as employed in said first expression system, and said co-suppressor wherein said co-suppressor comprises amino acid residues 1-1329 plus 1376-1495, as set forth in SEQ ID NO:1, or conservative amino acid variations thereof and, wherein said co-suppressor forms a complex with at least one member of the steroid/thyroid hormone superfamily of receptors, and thereafter selecting those compounds which provide:

increased reporter signal upon exposure of said compound to said second expression system, relative to reporter signal in the absence of said compound, and increased reporter signal upon exposure of said compound to said first expression system, relative to reporter signal in the absence of said compound, wherein said selected compounds are capable of relieving the suppression of steroid/thyroid hormone receptor activity caused by a co-suppressor of steroid/thyroid hormone receptor activity, said co-suppressor having a structure and function characteristic of the silencing mediator for retinoic acid and thyroid hormone receptors, and activating said receptor.

2. A method according to claim 1 wherein said mutant receptor is selected from TR160 homodimers or TR160-containing heterodimers.

3. A method according to claim 1, wherein the expression system is a mammalian or yeast cell.

4. A method to identify compounds which activate a steroict/thyroid hormone receptor, and disrupt the ability of a co-suppressor having a structure and function characteristic of a silencing mediator for retinoic acid and thyroid receptors to complex with said receptor, said method comprising:

determining the effect of a test compound on a reporter signal produced by a first expression system and on a reporter signal produced by a second expression system, wherein said first expression system comprises a complex comprising:

a modified co-suppressor, comprising amino acid residues 1-1329 plus 1376-1495 as set forth in SEQ ID NO: 1 or conservative amino acid variations thereof, plus a GAL4 activation domain, wherein said co-suppressor forms a complex with at least one member of the steroid/thyroid hormone superfamily of receptors a homodimeric or heterodimeric member of the steroid/thyroid hormone superfamily of receptors selected from thyroid hormone receptor homodimer, thyroid hormone receptor-retinoid X receptor heterodimer, retinoic acid receptor homodimer or retinoic acid receptor-retinoid X receptor heterodimer, and a response element for said member of the steroid/thyroid hormone superfamily of receptors, wherein said response element is operatively linked to a reporter, and wherein said second expression system comprises a complex comprising: said modified co-suppressor, the same homodimeric or heterodimeric member of the steroid/thyroid hormone superfamily of receptors as employed in said first expression system, wherein said mcanber is mutated such that it retains hormone dependent activation activity but has lost its ability to repress basal level promoter activity of target genes, and the same response element-reporter combination as employed in said first expression system, and thereafter selecting those compounds which provide:

a reduction in reporter signal upon exposure of compound to said first expression system, relative to reporter signal in the absence of said compound, and increased reporter signal upon exposure of compound to said second expression system, relative to reporter signal in the absence of said compound, wherein said selected compounds are capable of activating a steroid/thyroid hormone receptor and disrupting a complex comprising steroid/thyroid hormone receptor and a co-suppressor having a structure and function characteristic of the silencing mediator for retinoic acid and thyroid receptors.

5. A method according to claim 4, wherein the expression system is a mammalian or yeast cell.

* * * * *

SEQUENCE LISTING

<160> NUMBER OF SEQ ID NOS: 3

<210> SEQ ID NO 1
<211> LENGTH: 1495
<212> TYPE: PRT
<213> ORGANISM: Homo sapiens

<400> SEQUENCE: 1

```
Met Glu Ala Trp Asp Ala His Pro Asp Lys Glu Ala Phe Ala Ala Glu
1               5                   10                  15

Ala Gln Lys Leu Pro Gly Asp Pro Pro Cys Trp Thr Ser Gly Leu Pro
            20                  25                  30

Phe Pro Val Pro Pro Arg Glu Val Ile Lys Ala Ser Pro His Ala Pro
        35                  40                  45

Asp Pro Ser Ala Phe Ser Tyr Ala Pro Pro Gly His Pro Leu Pro Leu
    50                  55                  60

Gly Leu His Asp Thr Ala Arg Pro Val Leu Arg Pro Pro Thr Ile
65                  70                  75                  80

Ser Asn Pro Pro Pro Leu Ile Ser Ser Ala Lys His Pro Ser Val Leu
                85                  90                  95

Glu Arg Gln Ile Gly Ala Ile Ser Gln Gly Met Ser Val Gln Leu His
            100                 105                 110

Val Pro Tyr Ser Glu His Ala Lys Ala Pro Val Gly Pro Val Thr Met
        115                 120                 125

Gly Leu Pro Leu Pro Met Asp Pro Lys Lys Leu Ala Pro Phe Ser Gly
    130                 135                 140

Val Lys Gln Glu Gln Leu Ser Pro Arg Gly Gln Ala Gly Pro Pro Glu
145                 150                 155                 160

Ser Leu Gly Val Pro Thr Ala Gln Glu Ala Ser Val Leu Arg Gly Thr
                165                 170                 175

Ala Leu Gly Ser Val Pro Gly Ser Ile Thr Lys Gly Ile Pro Ser
            180                 185                 190

Thr Arg Val Pro Ser Asp Ser Ala Ile Thr Tyr Arg Gly Ser Ile Thr
        195                 200                 205

His Gly Thr Pro Ala Asp Val Leu Tyr Lys Gly Thr Ile Thr Arg Ile
    210                 215                 220
```

```
Ile Gly Glu Asp Ser Pro Ser Arg Leu Asp Arg Gly Arg Glu Asp Ser
225                 230                 235                 240

Leu Pro Lys Gly His Val Ile Tyr Glu Gly Lys Lys Gly His Val Leu
            245                 250                 255

Ser Tyr Glu Gly Gly Met Ser Val Thr Gln Cys Ser Lys Glu Asp Gly
            260                 265                 270

Arg Ser Ser Gly Pro Pro His Glu Thr Ala Ala Pro Lys Arg Thr
        275                 280                 285

Tyr Asp Met Met Glu Gly Arg Val Gly Arg Ala Ile Ser Ser Ala Ser
    290                 295                 300

Ile Glu Gly Leu Met Gly Arg Ala Ile Pro Pro Glu Arg His Ser Pro
305                 310                 315                 320

His His Leu Lys Glu Gln His His Ile Arg Gly Ser Ile Thr Gln Gly
                325                 330                 335

Ile Pro Arg Ser Tyr Val Glu Ala Gln Glu Asp Tyr Leu Arg Arg Glu
            340                 345                 350

Ala Lys Leu Leu Lys Arg Glu Gly Thr Pro Pro Pro Pro Pro Ser
        355                 360                 365

Arg Asp Leu Thr Glu Ala Tyr Lys Thr Gln Ala Leu Gly Pro Leu Lys
    370                 375                 380

Leu Lys Pro Ala His Glu Gly Leu Val Ala Thr Val Lys Glu Ala Gly
385                 390                 395                 400

Arg Ser Ile His Glu Ile Pro Arg Glu Glu Leu Arg His Thr Pro Glu
            405                 410                 415

Leu Pro Leu Ala Pro Arg Pro Leu Lys Glu Gly Ser Ile Thr Gln Gly
        420                 425                 430

Thr Pro Leu Lys Tyr Asp Thr Gly Ala Ser Thr Thr Gly Ser Lys Lys
        435                 440                 445

His Asp Val Arg Ser Leu Ile Gly Ser Pro Gly Arg Thr Phe Pro Pro
    450                 455                 460

Val His Pro Leu Asp Val Met Ala Asp Ala Arg Ala Leu Glu Arg Ala
465                 470                 475                 480

Cys Tyr Glu Glu Ser Leu Lys Ser Arg Pro Gly Thr Ala Ser Ser Ser
            485                 490                 495

Gly Gly Ser Ile Ala Arg Gly Ala Pro Val Ile Val Pro Glu Leu Gly
            500                 505                 510

Lys Pro Arg Gln Ser Pro Leu Thr Tyr Glu Asp His Gly Ala Pro Phe
        515                 520                 525

Ala Gly His Leu Pro Arg Gly Ser Pro Val Thr Met Arg Glu Pro Thr
    530                 535                 540

Pro Arg Leu Gln Glu Gly Ser Leu Ser Ser Ser Lys Ala Ser Gln Asp
545                 550                 555                 560

Arg Lys Leu Thr Ser Thr Pro Arg Glu Ile Ala Lys Ser Pro His Ser
            565                 570                 575

Thr Val Pro Glu His His Pro His Pro Ile Ser Pro Tyr Glu His Leu
            580                 585                 590

Leu Arg Gly Val Ser Gly Val Asp Leu Tyr Arg Ser His Ile Pro Leu
        595                 600                 605

Ala Phe Asp Pro Thr Ser Ile Pro Arg Gly Ile Pro Leu Asp Ala Ala
    610                 615                 620

Ala Ala Tyr Tyr Leu Pro Arg His Leu Ala Pro Asn Pro Thr Tyr Pro
625                 630                 635                 640
```

-continued

His Leu Tyr Pro Pro Tyr Leu Ile Arg Gly Tyr Pro Asp Thr Ala Ala
          645                 650                 655

Leu Glu Asn Arg Gln Thr Ile Ile Asn Asp Tyr Ile Thr Ser Gln Gln
            660                 665                 670

Met His His Asn Thr Ala Thr Ala Met Ala Gln Arg Ala Asp Met Leu
            675                 680                 685

Arg Gly Leu Ser Pro Arg Glu Ser Ser Leu Ala Leu Asn Tyr Ala Ala
        690                 695                 700

Gly Pro Arg Gly Ile Ile Asp Leu Ser Gln Val Pro His Leu Pro Val
705                 710                 715                 720

Leu Val Pro Pro Thr Pro Gly Thr Pro Ala Thr Ala Met Asp Arg Leu
                725                 730                 735

Ala Tyr Leu Pro Thr Ala Pro Gln Pro Phe Ser Ser Arg His Ser Ser
            740                 745                 750

Ser Pro Leu Ser Pro Gly Gly Pro Thr His Leu Thr Lys Pro Thr Thr
        755                 760                 765

Thr Ser Ser Ser Glu Arg Glu Arg Asp Arg Asp Arg Glu Arg Asp Arg
    770                 775                 780

Asp Arg Glu Arg Glu Lys Ser Ile Leu Thr Ser Thr Thr Thr Val Glu
785                 790                 795                 800

His Ala Pro Ile Trp Arg Pro Gly Thr Glu Gln Ser Ser Gly Ser Ser
                805                 810                 815

Gly Ser Ser Gly Gly Gly Gly Ser Ser Ser Arg Pro Ala Ser His
        820                 825                 830

Ser His Ala His Gln His Ser Pro Ile Ser Pro Arg Thr Gln Asp Ala
    835                 840                 845

Leu Gln Gln Arg Pro Ser Val Leu His Asn Thr Gly Met Lys Gly Ile
    850                 855                 860

Ile Thr Ala Val Glu Pro Ser Lys Pro Thr Val Leu Arg Ser Thr Ser
865                 870                 875                 880

Thr Ser Ser Pro Val Arg Pro Ala Ala Thr Phe Pro Pro Ala Thr His
            885                 890                 895

Cys Pro Leu Gly Gly Thr Leu Asp Gly Val Tyr Pro Thr Leu Met Glu
        900                 905                 910

Pro Val Leu Leu Pro Lys Glu Ala Pro Arg Val Ala Arg Pro Glu Arg
        915                 920                 925

Pro Arg Ala Asp Thr Gly His Ala Phe Leu Ala Lys Pro Pro Ala Arg
    930                 935                 940

Ser Gly Leu Glu Pro Ala Ser Ser Pro Ser Lys Gly Ser Glu Pro Arg
945                 950                 955                 960

Pro Leu Val Pro Val Ser Gly His Ala Thr Ile Ala Arg Thr Pro
            965                 970                 975

Ala Lys Asn Leu Ala Pro His His Ala Ser Pro Asp Pro Ala Pro
        980                 985                 990

Pro Ala Ser Ala Ser Asp Pro His Arg Glu Lys Thr Gln Ser Lys Pro
        995                 1000                1005

Phe Ser Ile Gln Glu Leu Glu Leu Arg Ser Leu Gly Tyr His Gly
    1010                1015                1020

Ser Ser Tyr Ser Pro Glu Gly Val Glu Pro Val Ser Pro Val Ser
    1025                1030                1035

Ser Pro Ser Leu Thr His Asp Lys Gly Leu Pro Lys His Leu Glu
    1040                1045                1050

Glu Leu Asp Lys Ser His Leu Glu Gly Glu Leu Arg Pro Lys Gln

-continued

```
            1055               1060                1065

Pro Gly Pro Val Lys Leu Gly Gly Glu Ala Ala His Leu Pro His
    1070                1075                1080

Leu Arg Pro Leu Pro Glu Ser Gln Pro Ser Ser Ser Pro Leu Leu
    1085                1090                1095

Gln Thr Ala Pro Gly Val Lys Gly His Gln Arg Val Val Thr Leu
    1100                1105                1110

Ala Gln His Ile Ser Glu Val Ile Thr Gln Asp Tyr Thr Arg His
    1115                1120                1125

His Pro Gln Gln Leu Ser Ala Pro Leu Pro Ala Pro Leu Tyr Ser
    1130                1135                1140

Phe Pro Gly Ala Ser Cys Pro Val Leu Asp Leu Arg Arg Pro Pro
    1145                1150                1155

Ser Asp Leu Tyr Leu Pro Pro Asp His Gly Ala Pro Ala Arg
    1160                1165                1170

Gly Ser Pro His Ser Glu Gly Gly Lys Arg Ser Pro Glu Pro Asn
    1175                1180                1185

Lys Thr Ser Val Leu Gly Gly Glu Asp Gly Ile Glu Pro Val
    1190                1195                1200

Ser Pro Pro Glu Gly Met Thr Glu Pro Gly His Ser Arg Ser Ala
    1205                1210                1215

Val Tyr Pro Leu Leu Tyr Arg Asp Gly Glu Gln Thr Glu Pro Ser
    1220                1225                1230

Arg Met Gly Ser Lys Ser Pro Gly Asn Thr Ser Gln Pro Pro Ala
    1235                1240                1245

Phe Phe Ser Lys Leu Thr Glu Ser Asn Ser Ala Met Val Lys Ser
    1250                1255                1260

Lys Lys Gln Glu Ile Asn Lys Lys Leu Asn Thr His Asn Arg Asn
    1265                1270                1275

Glu Pro Glu Tyr Asn Ile Ser Gln Pro Gly Thr Glu Ile Phe Asn
    1280                1285                1290

Met Pro Ala Ile Thr Gly Thr Gly Leu Met Thr Tyr Arg Ser Gln
    1295                1300                1305

Ala Val Gln Glu His Ala Ser Thr Asn Met Gly Leu Glu Ala Ile
    1310                1315                1320

Ile Arg Lys Ala Leu Met Gly Lys Tyr Asp Gln Trp Glu Glu Ser
    1325                1330                1335

Pro Pro Leu Ser Ala Asn Ala Phe Asn Pro Leu Asn Ala Ser Ala
    1340                1345                1350

Ser Leu Pro Ala Ala Met Pro Ile Thr Ala Ala Asp Gly Arg Ser
    1355                1360                1365

Asp His Thr Leu Thr Ser Pro Gly Gly Gly Gly Lys Ala Lys Val
    1370                1375                1380

Ser Gly Arg Pro Ser Ser Arg Lys Ala Lys Ser Pro Ala Pro Gly
    1385                1390                1395

Leu Ala Ser Gly Asp Arg Pro Pro Ser Val Ser Ser Val His Ser
    1400                1405                1410

Glu Gly Asp Cys Asn Arg Arg Thr Pro Leu Thr Asn Arg Val Trp
    1415                1420                1425

Glu Asp Arg Pro Ser Ser Ala Gly Ser Thr Pro Phe Pro Tyr Asn
    1430                1435                1440

Pro Leu Ile Met Arg Leu Gln Ala Gly Val Met Ala Ser Pro Pro
    1445                1450                1455
```

```
Pro Pro Gly Leu Pro Ala Gly Ser Gly Pro Leu Ala Gly Pro His
    1460            1465                1470

His Ala Trp Asp Glu Glu Pro Lys Pro Leu Leu Cys Ser Gln Tyr
    1475            1480                1485

Glu Thr Leu Ser Asp Ser Glu
    1490            1495

<210> SEQ ID NO 2
<211> LENGTH: 46
<212> TYPE: PRT
<213> ORGANISM: ARTIFICIAL
<220> FEATURE:
<223> OTHER INFORMATION: RESIDUES 1330-1376 OF SEQUENCE 1

<400> SEQUENCE: 2

Gly Lys Tyr Asp Gln Trp Glu Glu Ser Pro Pro Leu Ser Ala Asn Ala
1               5                   10                  15

Phe Asn Pro Leu Asn Ala Ser Ala Ser Leu Pro Ala Ala Met Pro Ile
            20                  25                  30

Thr Ala Ala Asp Gly Arg Ser Asp His Thr Leu Thr Ser Pro
            35                  40                  45

<210> SEQ ID NO 3
<211> LENGTH: 17
<212> TYPE: DNA
<213> ORGANISM: ARTIFICIAL
<220> FEATURE:
<223> OTHER INFORMATION: GAL4 RESPONSE ELEMENT palindromic

<400> SEQUENCE: 3
cggaggactg tcctccg                                              17
```